United States Patent [19]

Schnatterer et al.

[11] Patent Number: 5,576,463
[45] Date of Patent: Nov. 19, 1996

[54] PROCESS FOR THE PREPARATION OF 2-NITROBENZALDEHYDES

[75] Inventors: Albert Schnatterer; Helmut Fiege, both of Leverkusen, Germany

[73] Assignee: Bayer Aktiengesellschaft, Leverkusen, Germany

[21] Appl. No.: 398,228

[22] Filed: Mar. 3, 1995

[30] Foreign Application Priority Data

Mar. 10, 1994 [DE] Germany ............................ 44 08 007.7

[51] Int. Cl.$^6$ ..................................................... C07C 45/32
[52] U.S. Cl. ............................ 568/431; 568/424; 568/426
[58] Field of Search ..................................... 568/426, 431, 568/436, 424

[56] References Cited

U.S. PATENT DOCUMENTS

| | | |
|---|---|---|
| 3,996,289 | 12/1976 | Meyer . |
| 4,297,519 | 10/1981 | Ertel . |
| 4,335,052 | 6/1982 | Bernhardt et al. . |
| 4,463,195 | 7/1984 | Marti et al. . |
| 4,689,433 | 8/1987 | Foa et al. . |
| 4,721,821 | 1/1988 | Anderson . |
| 5,082,976 | 1/1992 | Blank et al. . |

OTHER PUBLICATIONS

Derwent Abstract of SE–A– 9 202 203 (Jan. 1994).
Derwent Abstract of JP 60–025957 (Feb. 8, 1985).
M. Hirano, et al, Bull. Chem. Soc. Jpn; vol. 63, pp. 2433–2434 (1990).
Clt. Comninellis et al; J. Appl Elelctrochem, vol. 9, pp. 753–755 (1979).

A. Banerjee, Indian J. Chem Sec. B, vol. 29B, pp. 257–262 (1990).

*Primary Examiner*—Samuel Barts
*Attorney, Agent, or Firm*—Sprung Horn Kramer & Woods

[57] ABSTRACT

The new process for the preparation of 2-nitrobenzaldehydes of the general formula

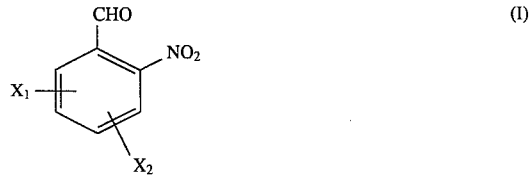

(I)

in which $X_1$ and $X_2$ either independently of one another represent hydrogen or halogen or one of the substituents represents nitro and the other substituent then represents hydrogen, by oxidation of 2-nitrotoluenes of the general formula

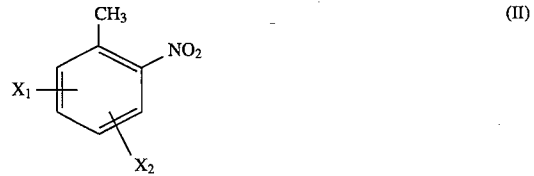

(II)

in which $X_1$ and $X_2$ have the meaning indicated above is characterized in that the oxidation with oxygen or an oxygen-containing gas is carried out in the presence of at least one alkoxyalkylamine as a solvent and in the presence of strong bases.

13 Claims, No Drawings

PROCESS FOR THE PREPARATION OF 2-NITROBENZALDEHYDES

The present invention relates to a process for the preparation of 2-nitrobenzaldehydes by oxidation of 2-nitrotoluenes with oxygen.

2-Nitrobenzaldehyes are important intermediates for pharmaceuticals. 2-Nitrobenzaldehyde, for example, is a starting material for the active compound nifedipine employed in coronary therapy.

A relatively large number of processes for the preparation of 2-nitrobenzaldehydes are already known. The most interesting processes from the economic point of view start from 2-nitrotoluene. 2-Nitrotoluene is available on a large scale and is a particularly inexpensive base material. As a deactivated derivative of toluene, 2-nitrotoluene, however, can only be expected to have a low reactivity towards an oxidative attack on the methyl group. In agreement with this statement, the direct oxidation of 2-nitrotoluene to 2-nitrobenzaldehyde has hitherto only been described with metals in high oxidation states as oxidizing agents, for example with Ce(IV) in perchloric acid as a solvent (cf. e.g. EP-A 205 173) or with electrochemically generated Co(III) in sulphuric acid as a solvent (cf. J. Appl. Elektrochem. 9 (1979), 96, 753–5). The stoichiometric use of metal compounds, however, is expensive as far as the material costs are concerned, and the process of electrochemical regeneration as well as the handling of relatively large amounts of these substances are complicated. Additionally, appreciable disposal or recycling costs can be expected with the solvents sulphuric acid and perchloric acid, completely apart from the safety problems in working with perchloric acid.

In order to avoid the low reactivity of 2-nitrotoluene towards oxidizing agents, in the past in many processes for the preparation of 2-nitrobenzaldehyde the circuitous route via the activation of the methyl group in the 2-nitrotoluene was taken. Thus, after reaction of the 2-nitrotoluene with bromine to give 2-nitrobenzyl bromide, the latter can be oxidized in good yields to 2-nitrobenzaldehyde, e.g. by reaction with dimethyl sulphoxide (cf. DE-A 2 808 930) or tertiary amine oxides (DE-A 2 948 058). Alternatively to this, the oxidation can also be carried out from the 2-nitrobenzyl alcohol stage, the hydrolysis product of 2-nitrobenzyl bromide, e.g. with $CrO_3$ (cf. Bull. Chem. Soc. Jpn. 63 (1990) 8, 2433–4) or $NH_4VO_3$ (cf. Indian J. Chem. Sect. B. 29B (1990) 3, 257–62).

Another possibility for the activation of the 2-nitrotoluene is based on derivatization by C-C linkage. By means of the reaction of 2-nitrotoluene with dimethylformamide acetal, 2-amino-o-nitrostyrene is obtained, which can be oxidized with oxygen under copper catalysis according to EP-A 430 001 or with sodium hypochlorite according to JP 60 025 957 to 2-nitrobenzaldehyde. Another variant of the C-C linkage and subsequent oxidation process is the reaction of 2-nitrotoluene with oxalic acid esters to give derivatives of pyruvic acid. The subsequent oxidation can be carried out, for example, with $H_2O_2$ according to EP-A 92 267 or with potassium permanganate according to DE-A 2 415 061.

The processes known hitherto for the preparation of 2-nitrobenzaldehyde based on 2-nitrotoluene have the disadvantage that oxidation either has to be carried out with metal compounds in perchloric acid or sulphuric acid or else multi-stage processes have to be tolerated. Reference was already made further above to the problems in working with metal compounds in perchloric acid or sulphuric acid. The disadvantages of multi-stage processes lie in the high plant and operating costs. Additionally, the multi-stage processes mentioned required expensive reaction components such as e.g. bromine or dimethylformamide acetal and in some cases also expensive oxidizing agents such as e.g. dimethyl sulphoxide, tertiary amine oxides or potassium permanganate.

A process was therefore needed which makes possible the preparation of the 2-nitrobenzaldehyde in a process which, if possible, is one-stage using an inexpensive oxidizing agent.

The invention relates to a process for the preparation of 2-nitrobenzaldehydes of the general formula

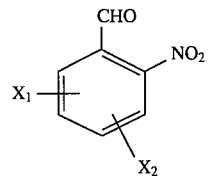
(I)

in which $X_1$ and $X_2$ either independently of one another represent hydrogen or halogen or one of the substituents represents nitro and the other substituent then represents hydrogen, by oxidation of 2-nitrotoluenes of the general formula

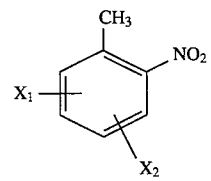
(II)

in which $X_1$ and $X_2$ have the meaning indicated above characterized in that the oxidation with oxygen or an oxygen-containing gas is carried out in the presence of at least one alkoxyalkylamine as a solvent and in the presence of strong bases.

Halogen in the definition of $X_1$ and $X_2$ preferably represents fluorine, chlorine or bromine. Examples which may be mentioned of 2-nitrotoluenes according to the definition in formula (II) which can be employed according to the invention are: 2-nitrotoluene, 4-fluoro-2-nitrotoluene, 4-chloro-2-nitrotoluene, 2,4-dinitrotoluene and 2,6-dinitrotoluene. The process according to the invention is particularly suitable for the oxidation of 2-nitrotoluene.

The alkoxyalkylamines employed as solvents for carrying out the process according to the invention preferably correspond to the formula

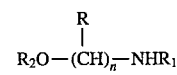
(III)

in which

R and $R_1$ independently of one another represent hydrogen or $C_1$–$C_4$-alkyl, $R_2$ represents $C_1$–$C_4$-alkyl and n represents 1 to 6.

Examples of the alkoxyalkylamines to be employed according to the invention are:

2-methoxyethylamine, 2-ethoxyethylamine, 3-methoxy-1-propylamine, 3-ethoxy-1-propylamine, 4-methoxy-1-butylamine, 4-methoxy-2-butylamine, N-methyl-2-methoxyethylamine, N-methyl-3-methoxy-1-propylamine and 2-methoxy-1-propylamine.

In a particular embodiment, a combination of at least one alkoxyalkylamine with at least one $C_1$–$C_4$-alcohol and/or $C_1$–$C_3$-diol and/or, if miscibility is assured, with water is employed as a solvent. The $C_1$–$C_4$-alcohol can be methanol, ethanol, 1-propanol, 2-propanol, 1-butanol, 2-butanol or tert-butanol; the $C_1$–$C_3$-diol includes 1,2-ethanediol, 1,2-propanediol and 1,3 -propanediol. The ratio of alkoxyalkylamine to the $C_1$–$C_4$-alcohol and/or $C_1$–$C_3$-diol and/or water is not subjected to any restriction and in general is determined by the solubility of the base in the reaction mixture and the reactivity of the 2-nitrotoluene employed. Normally, the alkoxyalkylamine moiety in the solvent mixture will be 30 to 95% by weight, preferably 50 to 95% by weight.

In particularly preferred manner, the process according to the invention is carried out in mixtures of alkoxyalkylamines of the formula $$R_3O\text{—}(CH_2)_n\text{—}NH_2 \qquad (IV)$$

in which $R_3$ represents methyl or ethyl and n represents 1–3, and methanol as a solvent.

Possible strong bases are alkali metal and alkaline earth metal compounds, for example metal hydroxides, metal alkoxides and metal amides and, if they are alkoxides and amides, of aluminium. Important alkali metals and alkaline earth metals which may be mentioned are, for example, sodium, potassium, lithium, calcium and magnesium. Alkoxides which may be mentioned are, for example, the methoxide, ethoxide, isopropoxide, 2-butoxide, tert-butoxide and the propylene glycolate. Among the bases mentioned, the hydroxides and alkoxides are preferred; sodium hydroxide and potassium hydroxide and sodium methoxide are particularly preferred. The bases mentioned can be employed individually or in any desired mixture with one another.

The strong base has only a catalytic function. Correspondingly, the oxidation of 2-nitrotoluenes to 2-nitrobenzaldehydes by the process according to the invention can be started even by the addition of catalytic amounts of the strong bases. Despite this, it may be advantageous in certain cases to employ stoichiometric or even above stoichiometric amounts of the strong bases. The amounts of the strong bases which are finally necessary depend on the particular reactivity of the 2-nitrotoluene of the formula (II) employed.

In general, the amount of the strong bases used can vary between 0.1 and 10 base equivalents per mole of 2-nitrotoluene, preferably between 0.2 and 5 base equivalents, particularly preferably between 0.2 and 3 base equivalents per mole of 2-nitrotoluene.

The selective oxidation of 2-nitrotoluenes to 2-nitrobenzaldehydes by treatment of 2-nitrotoluenes with oxygen in the presence of strong bases is a very unexpected reaction, as in the oxidation of toluenes such as e.g. toluene or xylene with oxygen normally the aldehyde formed rapidly reacts further to the corresponding benzoic acid under the reaction conditions and the aldehyde selectivity is correspondingly only very low. The reaction is moreover all the more surprising as according to EP-A 207 123 2,2'-dinitrobibenzyl and 4,4'-dinitrobibenzyl respectively are formed as main products on treatment of 2-nitrotoluene and of 4-nitrotoluene with oxygen in the presence of strong bases.

It can be advantageous to carry out the process according to the invention with the addition of a catalyst, but it is not absolutely necessary. The catalysts used are in particular transition metal compounds, for example of Co, Mn, Cr, Fe, Ni, Cu, V and Ru. Possible use forms of these metals are their inorganic acid salts, for example the metal fluorides, chlorides, sulphates, nitrates, carbonates and phosphates; the metal oxides and metal hydroxides; the organic acid metal salts, for example the metal acetates, oxalates, phenoxides, benzoates and salicylates; complexes of these metals, for example, with acetylacetone, N,N'-disalicylidene-ethylenediamine, tetraphenylporphine and phthalocyanine. Among the metal catalysts, the compounds of manganese are of particular interest.

The amount of metal catalyst can vary over a wide range. Normally, amounts used of 0.0001 to 0.05, preferably 0.0005 to 0.02 mol equivalents per mole of 2-nitrotoluene are sufficient. Of course, the catalytic effect of the metal catalysts can be utilized advantageously on use of larger amounts of metal catalyst.

The oxygen used as an oxidizing agent for the process according to the invention can be employed in pure form or in dilute form, for example in the form of oxygen-containing gases. The economically most favourable form of the oxygen to be employed according to the invention is atmospheric air. The pressure of the oxygen or of the oxygen-containing gas is not subjected to any particular restriction and can be between 0.5 and 20 bar, preferably between 0.8 and 10 bar, particularly preferably 0.8 to 3 bar. When using oxygen-containing gases, the oxygen content is likewise not subjected to any restriction.

The content and pressure of the oxygen-containing gas above all depends on the reaction rate and the selectivity obtainable. In the individual case, the most favourable conditions for introduction of gas can be determined by simple preliminary tests.

It is advantageous to disperse the oxygen or the air in the reaction mixture finely, for example using nozzles or frits. The oxygen or the air, however, can also be absorbed into the reaction mixture by vigorous stirring using suitable stirrers.

The reaction temperature for the process according to the invention can vary between $-50°$ C. and $+50°$ C. Preferably, however, the reaction is carried out at a temperature between $-30°$ and $+30°$ C.

The isolation of the 2-nitrobenzaldehydes from the reaction mixtures obtained in the process according to the invention is carried out by the known basic process operations such as, e.g. distillation or extraction, and primarily depends on the solvents used in the oxidation. If compounds having primary amino groups were employed in the oxidation as solvents, the 2-nitrobenzaldehydes are primarily present as aldehyde imines. The solvents can be removed from reaction mixtures of this type, for example, by distillation. If appropriate, it may be expedient to neutralize excess strong base with acids before removal of the solvents. The crude mixture after removal of the solvents is treated with water and catalytic amounts of mineral acid in order to hydrolyse any imines formed, and the 2-nitrobenzaldehyde is isolated, for example by distillation, steam distillation or extraction. The isolation and purification of the 2-nitrobenzaldehyde can also be carried out advantageously via the bisulphite adduct.

EXAMPLE 1

13.7 g of 2-nitrotoluene, 0.10 g of $MnSO_4 \cdot H_2O$ and 100 g of 2-methoxyethylamine were initially introduced into a 250 ml glass reactor at $-5°$ C. A solution of 6.6 g of KOH in 12 g of methanol was then metered in during the course of 1 h with introduction of pure oxygen into the solution under normal pressure. After addition of alkali was complete, oxidation was subsequently carried out for a further 3.5 h up to a total $O_2$ uptake of 2.0 1 and the excess alkali was then neutralized by addition of 80% strength sulphuric acid. The temperature in the reaction mixture was kept at −5° C. during the entire reaction. Product isolation began with the removal of the solvents 2-methoxyethylamine and methanol by distillation. The residue from the solvent distillation was treated with about 150 ml of water and acidified to pH 1 with 80% strength sulphuric acid, and the water phase was extracted three times with methylene chloride. The methylene chloride phase was dried over sodium sulphate and the solvent was removed by distillation. 14.3 g of dark-coloured oil remained as a residue, which according to GC analysis had a content of 20.8% of 2-nitrotoluene and 50.2% of 2-nitrobenzaldehyde.

| | |
|---|---|
| Conversion, 2-nitrotoluene: | 78.3% |
| Selectivity, 2-nitrobenzaldehyde: | 60.8% |

EXAMPLE 2

Procedure as Example 1 with the difference that oxidation was carried out at −10° C. and that 18.0 g of a 30% strength solution of sodium methoxide in methanol was metered in as the strong base. Discontinuation of reaction after uptake of 2.5 1 of $O_2$; reaction time 5.5 h. Working up as in Example 1:

| | |
|---|---|
| Crude product: | 15.2 g of dark-coloured oil |
| Conversion, 2-nitrotoluene: | 83% |
| Selectivity, 2-nitrobenzaldehyde: | 55.9% |

EXAMPLE 3

Procedure as Example 1 with the difference that the reaction was carried out at 0° C. without addition of $MnSO_4$ and that 35.0 g of a 30% strength solution of sodium methoxide in methanol was metered in as the strong base. Discontinuation of reaction after 4 h with a 2.5 1 $O_2$ uptake. Working up as in Example 1:

| | |
|---|---|
| Crude product: | 15.2 g of dark-coloured oil |
| Conversion, 2-nitrotoluene: | 92.1% |
| Selectivity, 2-nitrobenzaldehyde: | 40.4% |

EXAMPLE 4

Procedure as Example 1 with the difference that the 2-methoxyethylamine was replaced by 100 g of 3-methoxypropylamine. Discontinuation of reaction after 6 h with a 0.8 1 $O_2$ uptake.

Working up as in Example 1:

| | |
|---|---|
| Crude product: | 14.1 g of dark-coloured oil |
| Conversion, 2-nitrotoluene: | 30.0% |
| Selectivity, 2-nitrobenzaldehyde: | 62.3% |

EXAMPLE 5

Procedure as Example 1 with the difference that 2-methoxyethylamine was replaced by 100 g of 3-ethoxypropylamine and that oxidation was carried out at +5° C. Discontinuation of reaction after 5.5 h with a 0.9 1 $O_2$ uptake.

Working up as in Example 1:

| | |
|---|---|
| Crude product: | 14.4 g of dark-coloured oil |
| Conversion, 2-nitrotoluene: | 33.6% |
| Selectivity, 2-nitrobenzaldehyde: | 59.2% |

EXAMPLE 6

13.7 g of 2-nitrotoluene, 0.10 g of $MnSO_4 \times H_2O$ and 100 g of 2-methoxy ethylamine were initially introduced into a glass reactor at −15° C. 4.0 g of sodium hydroxide powder were added with introduction of pure oxygen into the mixture under normal pressure. After an induction period of a few minutes, the oxygen uptake started. The temperature of the reaction mixture was kept at −15° C. during the entire reaction. The reaction was stopped after 8 hours at an oxygen total uptake of 2.3 1 by neutralization of the excess alkali by addition of 80% by weight strength sulfuric acid. Working up as in Example 1.

| | |
|---|---|
| Crude product: | 15.4 g of dark-coloured oil |
| Conversion, 2-nitrotoluene: | 83.5% |
| Selectivity, 2-nitrobenzaldehyde: | 56,8%. |

We claim:
1. In the preparation of a 2-nitrobezaldehyde of the formula

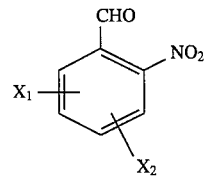
(I)

in which
  $X_1$ and $X_2$ each independently is hydrogen or halogen, or one is nitro and the other is hydrogen,
by oxidation of a 2-nitrotoluene of the formula

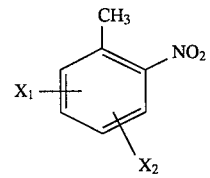
(II)

with an oxygen-containing gas, the improvement which comprises carrying out the reaction in the presence of at least one alkoxyalkylamine as a solvent and in the presence of at least one strong base selected from the group consisting of alkali metal and alkaline earth metal hydroxides, alkoxides and amides, aluminum alkoxides and amides.

2. The process according to claim 1, wherein the alkoxyalkylamine solvent of the formula

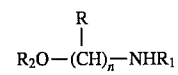
(III)

in which
  R and $R_1$ each independently is hydrogen or $C_1$–$C_4$-alkyl,
  $R_2$ is $C_1$–$C_4$-alkyl, and
  n is from 1 to 6.

3. The process according to claim 1, wherein the solvent further comprises at least one member selected from the group consisting of a $C_1$–$C_4$-alcohol, $C_2$–$C_3$-diol and water.

4. The process according to claim 2, wherein the solvent further contains methanol.

5. The process according to claim 1, wherein the strong base is present in from 0.1 to 10 equivalents per mole of 2-nitrotoluene.

6. The process according to claim 1, wherein the strong base is at least one member selected from the group consisting of a hydroxide, methoxide, ethoxide, isopropoxide, 2-butoxide, tert-butoxide or propylene glycolate of sodium, potassium, lithium, calcium or magnesium.

7. The process according to claim 1, wherein the strong base comprises at least one member selected from the group consisting of sodium hydroxide, potassium hydroxide and sodium methoxide, and is present in from 0.2 to 5 base equivalents per mole of 2-nitrotoluene.

8. The process according to claim 1, wherein the reaction is effected in the presence of at least one transition metal compound as catalyst.

9. The process according to claim 8, wherein the transition metal is selected from the group consisting of Co, Mn, Cr, Fe, Ni, Cu, V and Ru.

10. The process according to claim 8, wherein the transition metal is Mn and is present in 0.0001 to 0.05 mole per mole of 2-nitrotoluene.

11. The process according to claim 1, wherein $X_1$ and $X_2$ are hydrogen.

12. The process according to claim 1, wherein the reaction is effected at from −50° C. to 50° C.

13. The process according to claim 2, wherein $X_1$ and $X_2$ are hydrogen, solvent further contains methanol, the strong base comprises at least one member selected from the group consisting of sodium hydroxide, potassium hydroxide and sodium methoxide, and is present in from 0.2 to 3 base equivalents per mole of 2-nitrotoluene, the reaction is effected at from −30° C. to 30° C. in the presence of a compound of Mn as catalyst present in 0.005 to 0.02 mole per mole of 2-nitrotoluene.

* * * * *